United States Patent [19]

Chernack

[11] Patent Number: 4,844,885

[45] Date of Patent: Jul. 4, 1989

[54] FRANGIBLE CAPSULES CONTAINING COMPOSITION

[75] Inventor: Milton P. Chernack, West Hempstead, N.Y.

[73] Assignee: Production Previews, New York, N.Y.

[21] Appl. No.: 35,973

[22] Filed: Apr. 8, 1987

[51] Int. Cl.$^4$ ............................................. A61K 7/04
[52] U.S. Cl. ...................................... 424/61; 424/451; 424/455
[58] Field of Search ............................ 424/61, 451, 455; 252/174.13; 134/38

[56] References Cited

U.S. PATENT DOCUMENTS

| | | | |
|---|---|---|---|
| 3,472,675 | 10/1969 | Gordon et al. | 428/131 |
| 3,686,701 | 8/1972 | Charle et al. | 424/61 X |
| 3,691,270 | 9/1972 | Charle et al. | 424/401 |
| 3,729,569 | 4/1973 | Charle et al. | 424/401 |
| 3,864,294 | 2/1975 | Busch, Jr. | 424/61 X |
| 3,978,204 | 8/1976 | Charle et al. | 424/401 |
| 4,126,144 | 11/1978 | Duarte | 424/61 X |
| 4,158,053 | 6/1979 | Greene et al. | 424/61 |

*Primary Examiner*—Thurman K. Page
*Attorney, Agent, or Firm*—Cohen, Pontani & Lieberman

[57] ABSTRACT

A pressure-sensitive microcapsule-containing composition composed of a liquid phase capable of solidification which has substantially evenly dispersed therethroughout a multiplicity of microencapsulated droplets of a solvent phase. The shells of the microcapsule are rupturable under applied pressure for selectively releasing the solvent phase for dissolving the liquid phase after it has solidified.

6 Claims, No Drawings

FRANGIBLE CAPSULES CONTAINING COMPOSITION

FIELD OF THE INVENTION

This invention relates to a solidifiable composition having dispersed therein pressure-sensitive solvent-containing microcapsules which are rupturable upon mechanical manipulation and release the encapsulated solvent for dissolving the composition after it has solidified. Specifically, the invention pertains to nail enamel containing microencapsulated solvents therefore.

BACKGROUND ART

To remove nail enamel or polish, it is common to apply a solvent or solvent composition to the coated area with an applicator brush, cosmetic cotton or towel which have been impregnated with a solvent or solvent composition. These solvent compositions are normally marketed in small glass or plastic containers which are accompanied by common problems such as accidental breakage and problems associated with the opening and closing of the closure member such as leakage of the solvent composition into suitcases, handbags, onto furniture, carpets and clothing. In addition, nail polish remover and nail polish or enamel are always kept in separate containers, mostly not purchased together and often not carried together during travel. Thus, nail polish remover is often not immediately available when needed. Finally, solvent compositions packaged in open containers easily evaporate with unpleasant odor.

It is known to avoid some of the above-mentioned disadvantages by incorporating minute liquid-containing capsules into a sheet material, the entrapped or enveloped liquid being released upon the application of pressure. Thus, U.S. Pat. No. 3,472,675 discloses a self-wetting sheet material comprising perforations filled with a variety of encapsulated materials such as detergents, antiseptic agents, solvents, adhesives and polishing agents.

A fragrance dispenser in form of a sheet material carrying pressure-rupturable microcapsules containing an aroma chemical is disclosed in U.S. Pat. No. 3,640,692. Microencapsulated solvents for use in a nail polish removing composition separate from the nail polish is disclosed in U.S. Pat. No. 3,686,701. The microcapsules are not within the nail polish but are contained in various forms of separate carriers such as for example, creams, emulsions, paper napkins, fabrics or porous synthetic materials. Finally, microencapsulated makeup removing or treating compositions which are incorporated in a flexible support are described in U.S. Pat. No. 3,691,270. Thus, the heretofore described microencapsulated agents have always been used in combination with a carrier material such as a sheet material, powders, creams or the like. The microcapsules-containing support element has always been a unit distinct and separate from the material with which or upon which it is intended to act.

It is therefore among the objects of the present invention to provide a composition which obviates the above-mentioned disadvantages by integrally incorporating a microencapsulated solvent agent into the substance or material to be dissolved.

A particularly advantageous feature of the present invention is the incorporation into pressure-sensitive microcapsules of a solvent for nail enamel which, upon the application of external pressure or abrasion or other mechanical manipulation, will rupture and release the solvent for dissolving the nail enamel and facilitating the subsequent removal thereof.

SUMMARY OF THE INVENTION

The present invention relates to a composition containing a microencapsulated first liquid solvent phase which is substantially evenly dispersed within and capable of dissolving a second solidifiable phase. The two phases, as a liquid but solidifiable composition, are applied to a surface by brushing or spraying and subsequently allowed to dry to form a solid coating. The solvent phase-containing microcapules are pressure-sensitive and rupturable upon applied pressure, abrasive action, a combination of applied pressure and abrasion, or shear stress thereby causing the solvent phase to be released for dissolving the second phase after it has solidified. As the term is used herein, the liquid or solvent phase and the solidifiable phase of the present composition may each contain one or more components including suitable adjuvants such as perfumes, coloring agents, antibacterial and fungicidal agents, oils and the like.

Microencapsulation is a technique known in the art and is therefore not part of this invention separate and distinct from the claimed composition.

For purposes of this invention, it is important that the walls or shells of the microcapsules are thin enough to rupture upon mechanical manipulation such as the application of pressure or shear stress, but be sufficiently thick to prevent the release of the solvent during the intended use of the hardened composition. Moreover, it is critical that the walls of the microcapsules are formed of a material that withstands any chemical or physical attack by the components making up both, the solvent phase within the microcapsules and the surrounding, continuous solidifiable phase.

It is further important that the second or continuous phase throughout which the solvent-containing microcapsules are dispersed be solidifiable. For example, the solidifiable phase may be any polymeric material dissolved in a volatile solvent which, after evaporation of the solvent, hardens into a solid coating or mass with the microcapsule homogeneously dispersed therewithin. The present invention, therefore, comprises both, a liquid composition and dried composition of a liquid phase containing microcapsule homogeneously dispersed in a continuous, solidifiable phase.

A preferred embodiment of the present invention provides an integral, self-contained nail enamel/nail enamel removing agent. Minute, nail polish recover-containing capsules are preferable homogeneously dispersed within the nail polish. The nail polish is applied to the nail surface in known manner and allowed to harden. The nail polish is thereafter removed whenever desired by simply wiping the nail polish off with a cosmetic cotton or tissue, i.e. by applying sufficient pressure to cause the microcapsule to rupture and to release the solvent for dissolving the dried nail enamel.

Other objects, features, and advantages of the invention will become apparent to those skilled in the art from the following detailed description of a preferred embodiment of the invention.

DETAILED DESCRIPTION OF THE PRESENTLY PREFERRED EMBODIMENT

As herein before set forth, the present invention provides a pressure sensitive capsules-containing composition in liquid or dried form comprising a continuous, solidifiable phase having substantially evenly dispersed therethrough a multiplicity of microencapsulated droplets of a solvent, the microcapsule being rupturable under applied pressure for selectively releasing the solvent for dissolving the solidifiable phase afer solidification thereof.

Microencapsulation is well known as exemplified by the aforementioned art. Any suitable known method may be used to divide the solvent into minute liquid particles and to surround the solvent particles by rupturable enveloping walls. For example, urea-formaldehyde capsules may be prepared by forming and agitating a precondensate with the solvent phase. The urea-formaldehyde prcondensate condenses into minute microscopic solvent-containing capsules. Starch acid-ester may also be mixed with the solvent phase to form an emulsion which is thereafter spray-dried resulting in minute liquid solvent particles surrounded by starch acid-ester envelopes. In all microencapsulation methods, the core material is divided into minute particles which are surrounded by rupturable envelopes, membranes or shells of suitable material. Suitable encapsulating or shell-forming materials include, but are not limited to, dextrin, gelatin, gum arabic, casein, paraffin wax, natural waxes such as carnauba wax, bees wax, candelilla wax, Japan wax, acrylic resin, styrene-maleic acid, polyamide, polyethylene and polyethylene-ethyl cellulose mixtures, polyurethanes, polyesters, acetal homopolymers and copolymers, epoxy resins, cellulose acetophthalate, and polypropylene. Accordingly, any suitable wall material may be used provided the microcapsules formed therefrom are inert with respect to the action of both the entrapped solvent phase as well as the continuous solidifiable phase. In addition, the microcapsule must also be impermeable to the encapsulated material, thus preventing the premature release of the entrapped solvent phase. In case the drying of the solidifiable material requires the application of elevated temperatures, the microcapsule-forming material should be sufficiently stable to prevent the evaporation of the solvent phase. The diameter of the microcapsule is not critical to the invention and may range for from about 1 to about 1,000 microns although the average particle size will generally be below about 200 microns and preferably of from about 1 to about 100 microns, from about 5 to about 50 microns being presently particularly preferred. The microcapsule generally have a wall thickness of from about 1 to about 60nm. Like the diameter, the wall thickness of the microcapsule is not critical to the invention, but should be sufficiently thick to withstand normally applied pressure but sufficiently thin to allow rupture of the microcapsule when desired by mechanical manipulation.

As pointed out, the term solvent phase is understood to include more than one solvent and more than one additive such as fragrances, oils and the like. Hence, each microcapsule may contain more than one solvent and different capsules may contain different solvents having different properties. It is also not necessary that all microcapsules have the same wall thickness thus allowing, if desired, for the controlled sequential rupture of the microcapsule.

Suitable solvents include, but are not limited to, ethanol, acetone, ethyl acetate, isopropyl acetate, butyl acetate, amyl acetate, butyl propionate, ethyl lactate, butyl stearate and compound having a high boiling point such as ethylene glycol monoethylether and -valeroacetone. Water may also be used. Known additives include, but are not limited to, oils, perfumes, antibacterial agents and fungicidal agents, dyes, pigments and other coloring agents may also be added to either the solidifiable phase or the solvent phase or the solvent phase or the shell-forming material.

The total liquid solvent content of the microcapsules per square inch should be sufficient for dissolving the solidified phase and can generally vary between 60% by weight to 95% by weight of the total mass of the capsules.

After encapsulation of the solvent phase, which is effected in known manner, the microcapsules, containing the solvent or solvent mixture and optionally one or more of the above mentioned additives, are incorporated into the solidifiable phase.

As solidifiable phase, any material which fulfills the following condition may be utilized. First the material must by solidifiable, i.e. become semi-solid or solid upon application and may, for example, by a monomeric or polymeric material in a volatile solvent including water. Secondly, the solidifiable phase must not react with the material forming the shell of the microcapsules and thirdly, the solidifiable phase must be dissolved in the microencapsulated solvent phase. Preferably, the solidifiable phase hardens with a smooth surface. For ease of preparation of the composition and proper intermixing of the prepared microcapsules into the solidifiable phase, the density of the latter should be substantially equal to the density of the microcapsules. Of course, during the preparation of the composition, rupture of the liquid particles-containing envelopes or microcapsules must be avoided. Substantially equal densities of the microcapsules and the surrounding continuous solidifiable phase will thus assist even distribution of the former in the latter and help to avoid accidental rupture of the microcapsules during preparation of the composition.

The microcapsules are preferably evenly distributed throughout the solidifiable phase and may or may not be of the same color as the solidifiable phase. Preferable, however, the microcapsules are not or substantially not visible to the naked eye.

A particularly preferred solidifiable phase is nail enamel which, upon exposure to air, will harden into a solid, smooth coating in a relatively short time after it has been applied. The nail enamel may be colorless or may contain any of the known coloring agents including agents which cause a brilliant or metallic luster.

The various aspects and modifications of the present invention will be further made apparent by reference to the following examples which are understood to be illustrative only and in no way limitative of the present invention. Unless otherwise indicated, the amounts of the ingredients in the following examples refer to parts by weight.

EXAMPLE 1

A nail polish/microencapsulated solvent composition may be produced by dividing 49.8 parts of acetone, 50 parts of ethyl acetate and 0.2 parts of fragrance into minute liquid particles and by coating the particles with an acrylic resin envelope in accordance with any of the known microencapsulation processes.

40 parts of solvent phase containing microcapsules are introduced into and evenly dispersed throughout 100 parts of nail enamel. The microcapsules have a diameter of about 5 to about 50 microns.

The liquid nail enamel/microencapsulated solvent composition is then applied to a finger nail and allowed to dry. After hardening, the nail enamel is removed with a cosmetic cotton or tissue by applying a squeezing and/or abrading action to the coated nail.

EXAMPLE 2

A nail polish/microencapsulated solvent composition is produced by dividing 5 parts of castor oil, 60 parts of ethyl acetate and 34.8 parts diethylene glycol momoethyl ether and 0.2 parts of fragrance into minute liquid particles with an acrylic resin envelope in accordance with any of the known microencapsulation processes. 25 parts of solvent phase containing microcapsules are introduced into and evenly dispersed throughout 100 parts of nail enamel. The microcapsule have a diameter of about 5 to about 50 microns.

The liquid nail enamel/microencapsulated solvent composition is then applied to a fingernail and allowed to dry. After hardening, the nail enamel is removed with a cosmetic cotton or tissue by applying a squeezing and/or abrading action to the coated nail.

The invention may be embodied in other specific forms without departing from the spirit or essential characteristics thereof. The present embodiments are therefore to be construed in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A pressure-sensitive microcapsules-containing composition comprising a nail enamel as a liquid solidifiable phase having substantially evenly dispersed therethroughout a multiplicity of microencapsulated droplets of a solvent phase comprising oil and/or fragrance, the walls of said microcapsules being rupturable under applied pressure for selectively releasing said solvent phase for dissolving said nail enamel after solidification thereof, said nail enamel and said solvent phase being non-reactive with said capsule walls.

2. A pressure-sensitive microcapsules containing composition comprising water soluble paint as a liquid solidifiable phase having substantially evenly dispersed therethroughout a multiplicity of microencapsulated droplets of an aqueous phase, the walls of said microcapsules being rupturable under applied pressure for selectively releasing said aqueous phase for dissolving said water soluble paint after solidification thereof, said aqueous phase and said water soluble paint being non-reactive with said capsule walls.

3. The composition of claim 1, wherein the microcapsules are substantially invisibly dispersed throughout the liquid phase.

4. The composition of claim 1, wherein the liquid phase forms a substantially smooth surface upon solidification thereof.

5. The composition of claim 1, wherein the microcapsules are of a size so as to not substantially interfere with the smooth appearance of the surface.

6. The composition of claim 1, wherein the solvent phase comprises at least two solvents.

* * * * *